(12) United States Patent
Carniato et al.

(10) Patent No.: US 6,277,845 B1
(45) Date of Patent: Aug. 21, 2001

(54) HYDRAZONO-BENZAZULENE DERIVATIVES, PHARMACEUTICAL COMPOSITIONS AND INTERMEDIATES

(75) Inventors: Denis Carniato, Cagnes Sur Mer (FR); Thomas R. Gadek, Oakland, CA (US); Francois Goubet, Paris; Jean-Francois Gourvest, Claye-Souilly, both of (FR); Jochen Knolle, Kriftel (DE); Robert S. McDowell, San Francisco, CA (US); Karl-Heinz Scheunemann, Liederbach (DE)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/509,263
(22) PCT Filed: Sep. 23, 1998
(86) PCT No.: PCT/FR98/02039
§ 371 Date: Jul. 7, 2000
§ 102(e) Date: Jul. 7, 2000
(87) PCT Pub. No.: WO99/15507
PCT Pub. Date: Apr. 1, 1999

(30) Foreign Application Priority Data

Sep. 24, 1997 (FR) .................................................. 97/11859

(51) Int. Cl.$^7$ .......................... C07D 233/50; C07C 25/84; A61K 31/15; A61K 31/4168; A61P 19/10
(52) U.S. Cl. .......................... 514/218; 514/218; 514/272; 514/275; 514/303; 514/318; 514/392; 540/492; 540/553; 544/321; 544/330; 544/332; 546/118; 548/302.7; 548/307.4; 548/321.5; 548/332.5; 558/41; 558/234; 560/10

(58) Field of Search ..................................... 514/392, 218, 514/272, 275, 303, 388; 548/332.5, 302.7, 307.4, 321.5; 558/41, 234; 560/10; 568/164, 326; 546/118; 544/321, 330, 332; 540/492, 553

(56) References Cited

FOREIGN PATENT DOCUMENTS

729933 A1 * 9/1996 (EP) .
96/06087 * 2/1996 (WO) .

* cited by examiner

Primary Examiner—Mukund J. Shah
Assistant Examiner—Thomas C McKenzie
(74) Attorney, Agent, or Firm—Bierman, Muserlian and Lucas

(57) ABSTRACT

Compounds of the formula

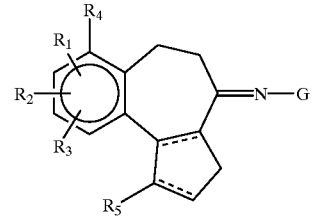

I wherein the substituents are as defined in the application and their pharmaceutically acceptable acid and base salts thereof which are useful for preventing loss of bone matrix.

20 Claims, No Drawings

HYDRAZONO-BENZAZULENE DERIVATIVES, PHARMACEUTICAL COMPOSITIONS AND INTERMEDIATES

This application is a 371 of PCT/FR98/02039 filed Sep. 23, 1998.

The present invention relates to novel tricyclic compounds, their preparation process and the intermediates of this process, their use as medicaments and the pharmaceutical compositions containing them.

A subject of the present invention is the compounds of general formula (I):

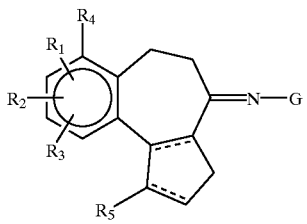

in which
- $R_1$ represents an —S(O)$_x$—[A]—[B]—COR$_6$ group, x being equal to 0, 1 or 2, —[A]— representing a divalent radical derived from a linear or branched, saturated or unsaturated acyclic hydrocarbon comprising 1 to 12 carbon atoms,
- [B] representing a phenyl radical, a CH(Z) radical, or a single bond,
- (Z) represents a hydrogen atom, a (D)$_{0-6}$—NRaRb, (D)$_{0-6}$—NH—SO$_2$—Rc, (D)$_{0-6}$—NH—CO$_2$—Rc, (D)$_{0-6}$—NH—CO—Rc, (D)$_{0-6}$—NH—SO$_2$—NH—Rc, (D)$_{0-6}$—NH—CO—NH—Rc, (D)$_{0-6}$—CO$_2$—Rc, (D)$_{0-6}$—SO$_2$—Rc, (D)$_{0-6}$—CO—Rc or (D)$_{0-6}$—Rc group in which (D)$_{0-6}$ is a divalent radical derived from a linear or branched, saturated or unsaturated acyclic hydrocarbon comprising 0 to 6 carbon atoms,
- Ra, Rb and Rc represent a hydrogen atom, a (CH$_2$)$_{0-3}$-Ar radical in which Ar represents a carbocyclic aryl group containing 6 to 18 carbon atoms, a (CH$_2$) 0-3—Het radical in which Het represents a radical derived from an aromatic or non aromatic, saturated or non saturated heterocycle comprising 1 to 9 carbon atoms and 1 to 5 heteroatoms chosen from oxygen, nitrogen or sulphur atoms, a (CH$_2$)$_{0-3}$-Alk radical in which Alk represents a radical derived from a non aromatic, linear, branched or cyclic, saturated or unsaturated hydrocarbon and comprising 1 to 12 carbon atoms, the Het, Ar and Alk radicals being able to be non substituted or substituted, or also, Ra and Rb represent together with the nitrogen atom to which they are linked a nitrogenous, aromatic or non aromatic, saturated or unsaturated heterocycle, optionally containing one or more heteroatoms chosen from oxygen, nitrogen or sulphur atoms, this radical being able to be substituted or non substituted,
- $R_6$ represents a hydroxyl radical, an O-Alk, O-Ar, NH$_2$, NH-Alk, N(Alk)$_2$ radical or the remainder of an L or D amino acid, Alk and Ar being as defined previously and being able to be substituted or non substituted,
- $R_2$ and $R_3$ identical or different represent either a hydrogen atom, a hydroxyl radical, an O-Alk radical or an O—(CH$_2$)$_{0-3}$-Ar radical, Alk and Ar being as defined previously, or $R_2$ and $R_3$ form together a ring of —O—(CRdRe)$_n$—O—type, n being an integer from 1 to 5, Rd and Re independently of each other represent a hydrogen atom, an alkyl radical containing 1 to 6 carbon atoms, or a phenyl radical,
- $R_4$ represents a hydrogen atom, a halogen atom, a hydroxyl, amino, nitro, cyano, CF$_3$, acyl or acyloxy group containing 1 to 12 carbon atoms alkyl, alkenyl, alkynyl, alkylthio, alkoxy, alkylamino, dialkylamino, dialkylaminoalkyl, dialkylaminoalkyloxy group, in which the term alkyl contains 1 to 6 carbon atoms,
- $R_5$ represents a hydrogen atom, a hydroxyl radical, a halogen atom, an O-Alk radical or an O—(CH$_2$)$_{0-3}$-Ar radical, Alk and Ar being as defined previously,
- G represents, either a radical of formula G1

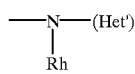

in which Rh is a hydrogen atom or an (Alk) group as defined previously and (Het') is a heterocycle of general formula:

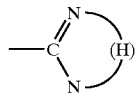

in which (H) forms, with the N=C—NH— unit, the remainder of a aromatic or non aromatic, mono- or bicyclic, heterocycle comprising 1 to 9 carbon atoms and 2 to 5 heteroatoms chosen from oxygen, nitrogen and sulphur atoms, this radical being able to be substituted or non substituted,
- or an NRaRb radical (radical G2), Ra and Rb being as defined above,
- or a (Het) radical (radical G3) as defined above,
- or an —NRh—C(=X)—NHRc radical (radical G4), in which X is a sulphur, oxygen atom or NH, Rh and Rc are as defined previously,
- or an —NRh—SO$_2$Rc radical, (radical G5), in which Rh and Rc are as defined previously, the dotted lines represent an optional second bond, as well as the addition salts with acids, bases and esters, $R_1$, $R_2$ and $R_3$ can be in position 8, 9 or 10 of the tricycle.

By compound of formula (I) is designated all the possible geometric isomers and stereoisomers taken individually or in a mixture.

When —[A]— represents a divalent radical derived from a linear or branched, saturated or unsaturated acyclic hydrocarbon comprising 1 to 12 carbon atoms, the alkylene radicals of formula —(CH$_2$)$_n$—, in which n represents an integer comprised between 1 and 12, such as —CH$_2$—, —CH$_2$CH$_2$—, —CH$_2$CH$_2$CH$_2$— or —CH$_2$CH$_2$CH$_2$CH$_2$—, or the alkenylene or alkynylene radicals such as —CH=CH—CH$_2$— or —C≡C—CH$_2$— are designated in particular.

When these divalent radicals are branched, it can be radicals such as —CH(CH$_3$)—, —C(Me)$_2$, —CH$_2$—C(Me)$_2$—, —CH (Et)—, —CH(C≡CH)— or —C(C≡—CH)(Et)—.

When [B] represents a divalent radical —Ph—, the COR$_6$ group can be in ortho, meta or para position. Preferably it is in para position.

When (D)$_{0-6}$ is a divalent radical derived from a linear or branched, saturated or unsaturated acyclic hydrocarbon comprising 0 to 6 carbon atoms, $(D)_{0-6}$ is chosen from the values of [A] mentioned above. By $(D)_0$ is meant the absence of this radical which reverts to having a single covalent bond. (D) will preferably be a single bond or a $(CH_2)_n$ group, n being an integer chosen from 1, 2 or 3.

When Ra, Rb and Rc represent a $(CH_2)_{0-3}$-Ar, $(CH_2)_{0-3}$—Het, $(CH_2)_{0-3}$-Alk group, $(CH_2)_{0-3}$ represents either a single bond in the case of $(CH_2)_0$, or the —$CH_2$—, —$(CH_2)_2$— or —$(CH_2)_3$— radicals.

By the term (Ar) representing a carbocyclic aryl group containing 6 to 18 carbon atoms, is meant a radical derived from an aromatic cyclic hydrocarbon such as the phenyl, naphthyl, phenanthrenyl radical or a radical derived from a condensed bicyclic or tricyclic hydrocarbon comprising a benzene ring such as indanyl, indenyl, dihydronaphthyl, tetrahydronaphthyl or fluorenyl. The junction is carried out at the level of the benzene ring. It is preferably phenyl.

By the term (Het) representing a radical derived from an aromatic or non aromatic, saturated or non saturated heterocycle, comprising 1 to 9 carbon atoms and 1 to 5 heteroatoms chosen from oxygen, nitrogen and sulphur atoms, is designated in particular:

heterocyclic monocyclic radicals, for example the thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl radicals, heterocyclic condensed rings, for example benzofurannyl, benzothienyl, benzimidazolyl, benzothiazolyl, naphtho[2,3-b]thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also polycyclic condensed systems constituted by heterocyclic monocyclics as defined above such as for example furo[2,3-b]pyrrole or thieno[2,3-b]furan, or saturated heterocycles such as pyrrolidine, piperidine, morpholine.

This term (Het) includes moreover the values of (Het') as defined previously.

By the term (Alk) representing a radical derived from a non aromatic, linear, branched or cyclic, saturated or unsaturated hydrocarbon, is designated in the case of acyclic hydrocarbons alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethylheptyl or n-decyl, alkenyl radicals such as vinyl, propenyl, isopropenyl, allyl, 2-methylallyl, butenyl or isobutenyl, or alkynyl radicals such as ethynyl, propynyl, propargyl, butynyl or isobutynyl, and in the case of cyclic radicals, cycloalkyl radicals, such as cyclopropyl, cyclobutyl, cyclopentyl, cyclohexyl or adamantyl.

When Ra and Rb represent together with the nitrogen atom to which they are linked a nitrogenous heterocycle, it is in particular the following saturated heterocycles morpholine, piperidine, piperazine, pyrrolidine, or unsaturated heterocycles such as pyrimidine, pyridine or pyrazine.

When $R_2$, $R_3$, $R_4$ and $R_5$ represent an O-(Alk) radical containing 1 to 12 carbon atoms, it is preferably methoxy, ethoxy, propyloxy, isopropyloxy, butyloxy, allenyloxy or propargyloxy radicals. When $R_2$, $R_3$, $R_4$ and $R_5$ represent an O—$(CH_2)_{0-3}$-Ar radical phenylethoxy and phenylpropyloxy radicals are preferably meant.

When $R_2$ and $R_3$ form together a ring of —O—$(CRdRe)_n$—O— type, n being an integer from 1 to 5, it is in particular the —O—$CH_2$—O, O—$C(Me)_2$—O, O—$C(Ph)_2$—O, O—$C(CH_3)$ (Ph)—O radicals, $R_2$ and $P_3$ are imperatively in ortho position relative to each other.

When $R_6$ represents an O-Alk or O-Ar radical, Alk and Ar being substituted or non substituted, it is in particular the following radicals: $(C_1-C_8)$ alkoxy, $(C_1-C_{14})$-aryl $(C_1-C_8)$-alkoxy, $(C_6-C_{14})$ aryloxy, $(C_1-C_8)$ alkylcarboxyloxy, $(C_1-C_8)$ dialkylaminocarbonylmethoxy, $(C_6-C_{14})$ aryl $(C_1-C_8)$ dialkylaminocarbonylmethoxy.

When $R_6$ represents an NH-alk, $NH(alk)_2$ or NH-Ar radical, it is in particular the $(C_1-C_8)$ alkylamino, di-$(C_1-C_8)$ alkylamino, $(C_6-C_{14})$ aryl $(C_2-C_8)$ alkylamino, $(C_6-C_{14})$ arylamino radicals.

When $R_6$ represents the remainder of an amino acid it can be L or D amino acid.

The L or D amino acids can be natural or not natural. Preferably it is α-amino acids. For example, those described in Houben-Weyl, Methoden der organischen Chemie, Band XV/1 and 2, Georg Thieme Verlag, Stuttgart, 1974:

Aad, Abu, γAbu, Abz, 2ABz, εAca, Ach, Acp, Adpd, Ahb, Aib, βAib, Ala, βAla, Δala, Alg, All, Ama, Amt, Ape, Apm, Apr, Arg, Asn, Asp, Asu, Aze, Azi, Bai, Bph, Can, Cit, Cys, $(Cys)_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hpro, hSer, hThr, hTrp, hTyr, Hyl, Hyp, 3Hyp, Ile, Ise, Iva, Kyn, Lant, Lcn, Leu, Lsg, Lys, βLys, Δlys, Met, Mim, Min, nArg, Nle, Nva, Oly, Orn, Pan, Pec, Pen, Phe, Phg, Pic, Pro, Δpro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), Neopentylglycine (Npg), Cyclohexylglycine (Chg), Cyclohexylalanine (Cha), 2-Thienylalanine (Thia), 2,2-diphenylaminoacetic acid, 2-(p-tolyl) 2-phenylamino acetic acid, 2-(p-chlorophenyl)amino acetic acid, or also 2-pyrrolidine acetic acid, 1,2,3,4-tetrahydroisoquinoline 3-acetic acid, decahydroisoquinoline 3-acetic acid, octahydroisoindol 2-acetic acid, decahydroquinoline 2-acetic acid, octahydrocyclopenta [b]pyrrol 2-carboxylic acid, 2-azabicyclo[2,2,2]octan-3-carboxylic acid, 2-azabicyclo[2,2,1]heptan-3-carboxylic acid, 2-azabicyclo[3,1,0]hexan-3-carboxylic acid, 2-azaspiro[4,4]nonan-3-carboxylic acid, 2-azaspiro[4,5]decan-3-carboxylic acid, spiro (bicyclo[2,2,1]heptan)-2,3-pyrrolidin-5-carboxylic acid, spiro (bicyclo[2,2,2]octan-2,3-pyrrolidin-5-carboxylic acid, 2-azatricyclo[4,3,0,1$^{6,9}$]decan-3-carboxylic acid, decahydrocyclohepta[b]pyrrol-2-carboxylic acid, decahydrocycloocta[c]pyrrol-2-carboxylic acid, octahydrocyclopenta[c]pyrrol-2-carboxylic acid, octahydroisoindol-1-carboxylic acid, 2,3,3a,4,6a-hexahydrocyclopenta[b]pyrrol-2-carboxylic acid, 2,3,3a,4,5,7a-hexahydroindol-2-carboxylic acid, tetrahydrothiazol-4-carboxylic acid, isoxazolidin-3-carboxylic acid, pyrazolidin-3-carboxylic acid, hydroxypyrrolidin-2-carboxylic acid, which if appropriate, can be substituted (see the following formulae):

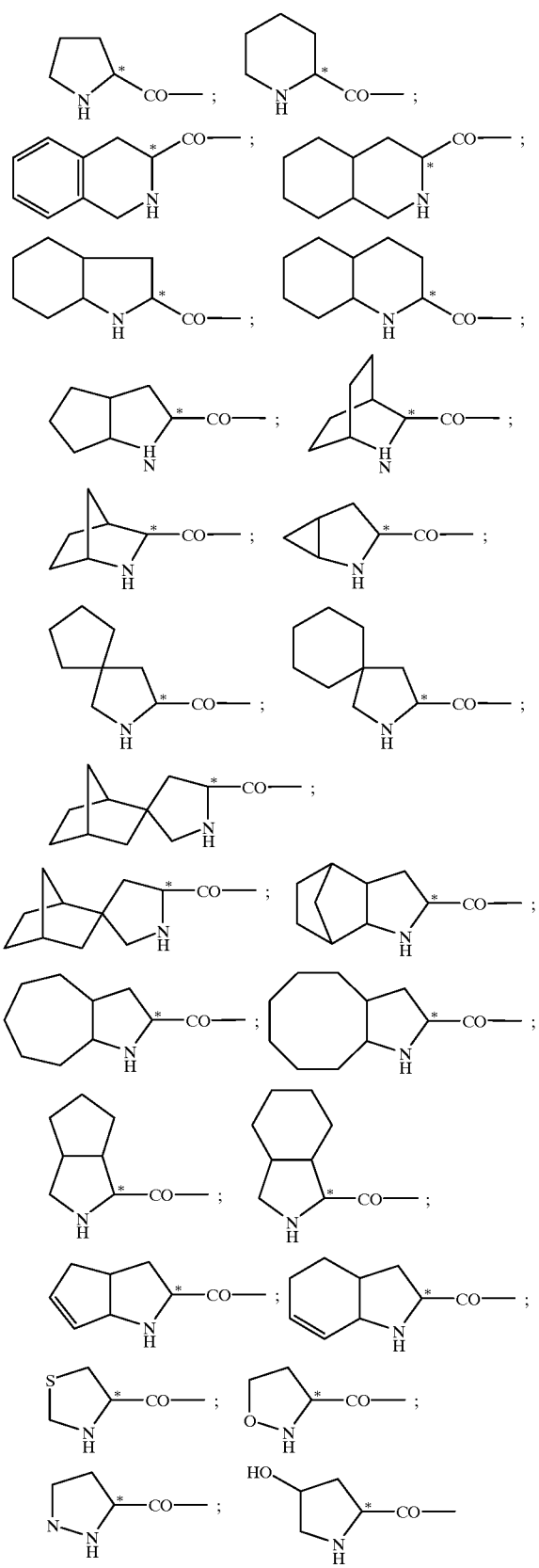

The heterocycle remainders described above are known, for example, in the following Patents or Patent Applications:

U.S. Pat. Nos. 4,344,949; 4,374,847; 4,350,704; EP-A-29.488; EP-A-31.741; EP-A-46.953; EP-A-49.605; EP-A-49.658; EP-A-50.800; EP-A-51.020; EP-A-52.870; EP-A-79.022; EP-A-84.164; EP-A-89.637; EP-A-90.341; EP-A-90.362; EP-A-105.102; EP-A-109.020; EP-A-111.873; EP-A-271.865 and EP-A-344.682.

Moreover the amino acids can be in the form of an ester or an amide, such as for example, methyl ester, ethyl ester, isopropyl ester, isobutyl ester, tert-butyl ester, benzyl ester, ethylamide, semicarbazide or ω-amino $(C_2-C_8)$—alkylamide.

Finally, the functional groups of these amino acids can be protected. The appropriate protective groups such as the protective groups of urethanes, the protective groups of carboxyl or the protective groups of the side chains are described by Hubbuch, Kontakte (Merck) 1979, No. 3, p. 14–23 and by Bullesbach, Kontakte (Merck) 1980, No. 1, p. 23–35.

For example Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tertbutyl, Obzl, Onbzl, Ombzl, Bzl, Mob, Pic, Trt can be mentioned.

When G is a radical of formula G1

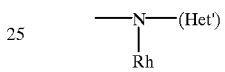

and (Het') is a heterocycle of general formula:

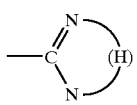

in which (H) forms, with the N=C—NH— unit, an aromatic or non aromatic, mono or bicyclic, saturated or non saturated heterocycle, comprising 1 to 9 carbon atoms and 2 to 5 heteroatoms chosen from oxygen, nitrogen and sulphur atoms, this radical being able to be substituted or non substituted, G1 represents in particular the following heterocycles:

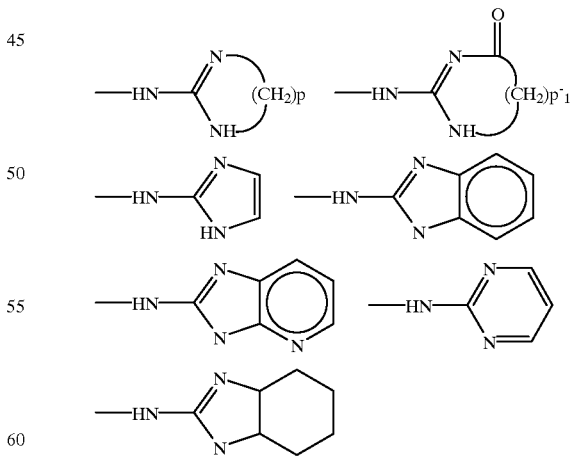

in which p represents an integer from 1 to 4.

When G is an —NRaRb radical (called G2), Ra and Rb can be a hydrogen atom, a $(CH_2)_{0-3}$-Ar, $(CH_2)_{0-3}$—Het or $(CH_2)_{0-3}$-Alk radical. The Ar, Het and Alk groups can also be substituted by the groups as defined below.

G2 can be in particular an NH₂, NH-Alk such as NHMe, NHEt, N(Alk)₂ such as NMe₂, NEt₂, NMeEt, NH—(CH₂)₀₋₁-Ar such as NHPh, NHCH₂Ph or NHCH₂Het such as NHCH₂-pyrrol-2-yl group.

When Ra is a hydrogen atom or an (Alk) group and when Rb is a (Het') group, the values of G1 are found.

When Ra and Rb form together with the nitrogen atom to which they are linked a nitrogenous heterocycle, it is in particular the heterocyclic groups described above, these being able to be substituted or non substituted.

When G is a (Het) radical (radical G3) this radical being able to be substituted or non substituted, it is in particular the heterocycles listed above and in particular the heterocycles of general formula (Het') as defined above. When this heterocycle is linked at the level of its nitrogen atom, the values of G2 are found in which Ra and Rb form a heterocycle with the nitrogen atom which carries them.

When G is an —NRh—C(=X)—NHRc radical (radical G4), or NRhSO₂Rc radical (radical G5), in which X is a sulphur, oxygen or NH atom, Rh and Rc are as defined previously. It is in particular the —NH—C (=NH)—NH₂, —NH—C(=O)—NH₂ or —NH—C (=S)—NH₂, —NH—C(=NH) —NHCH₂-Ar such as —NH—C(=NH) —NHCH₂Ph, —NH—C(=NH)—NHCH₂—Het, —NH—C(=NH) —NHCH₂—Het', —NH—C(=NH) —NH-Alk such as —NH—C (=NH)—NHCH₃, or —NH—SO₂Ph groups, the Ar, Het, Het' or Alk groups being substituted or non substituted.

The optional substituents of the (Alk), (Ar), (Het), (Het') or NRaRb radicals forming a heterocycle, are preferably the following radicals:

halogen: fluorine, chlorine, bromine, iodine, alkyl, alkenyl, alkynyl containing 1 to 12 carbon atoms such as methyl, ethyl, propyl, isopropyl, butyl, isobutyl, tert-butyl, vinyl or allenyl. These radicals being themselves optionally substituted by one or more halogen atoms, for example fluorine such as trifluoromethyl, oxo, cyano, nitro, formyl, carboxy and carboxyalkyl containing 1 to 6 carbon atoms, carboxamide, alkoxy containing 1 to 12 carbon atoms such as methoxy, ethoxy, propyloxy, isopropyloxy, butyloxy, alkylthio containing 1 to 12 carbon atoms such as methylthio, ethylthio, propylthio, isopropylthio, butylthio, amino, alkylamino containing 1 to 12 carbon atoms such as methylamino or ethylamino, dialkylamino containing 2 to 24 carbon atoms such as dimethylamino, diethylamino, methylethylamino, each of these dialkylamino radicals being optionally in oxidized form, aminoalkyl containing 1 to 12 carbon atoms such as aminomethyl or aminoethyl, dialkylaminoalkyl containing 3 to 25 carbon atoms such as dimethylamino methyl or ethyl, dialkylaminoalkyloxy containing 3 to 25 carbon atoms such as dimethylaminoethyloxy, optionally acylated hydroxyl containing 1 to 12 carbon atoms, for example acetoxy, acyl containing 1 to 12 carbon atoms such as formyl, acetyl, propionyl, butyryl, isobutyryl, valeryl, isovaleryl, succinyl, pivaloyl benzoyl optionally substituted for example by a chlorine, iodine or fluorine atom. The chloroacetyl, dichloroacetyl, trichloroacetyl, bromoacetyl or trifluoroacetyl radicals can be mentioned, carbocyclic or heterocyclic aryl such as phenyl, furyl, thienyl, pyridinyl or aralkyl such as benzyl, these radicals themselves being optionally substituted by the halogen, alkyl, alkoxy, alkylthio, amino alkyl or dialkylamino radicals indicated above.

When Ar represents a phenyl, this can be substituted by an O—(CRdRe)ₙ—O group as defined previously.

Of course, one or more substituents, identical or different, can be present. In the case of (Het) the substituents can be at the level of the NH group or of the carbon atom.

These substituents also illustrate the definition of R₄.

It is of course understood that when R₁, R₂, R₃, R₄, R₅, R₆, Rₐ, R_b, R_c represent an alkyl, aryl or heterocycle group as defined above, they can be identical or different independently of each other.

The invention naturally extends to the salts of the compounds of formula (I), such as for example the salts formed when the compounds of formula (I) comprise an amino or amino guanidine function, with the following acids: hydrochloric, hydrobromic, nitric, sulphuric, phosphoric, acetic, trifluoroacetic, formic, propionic, benzoic, maleic, fumaric, succinic, tartaric, citric, oxalic, glyoxylic, aspartic, alkanesulphonic acids such as methane or ethanesulphonic acids, arenesulphonic acids, such as benzene or paratoluene sulphonic acids and arylcarboxylic acid, or when the compounds of formula (I) comprise an acid function, with the salts of alkali or alkaline-earth metals or of ammonium optionally substituted.

The invention also extends to the esters of the compounds of formula (I).

In a first preferred group, a subject of the invention is the compounds of general formula (I) as defined previously, corresponding to general formula (I'):

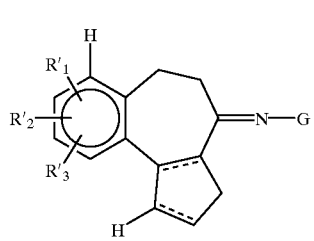

(I')

represents an

—S(O)ₓ—[A']—[B']—COR'₆ group, x being equal to 0, 1 or 2, —[A']— representing a divalent alkylene, alkenylene or alkynylene radical containing 2 to 6 carbon atoms, [B'] representing a CH(Z') radical or a single bond, (Z') represents a hydrogen atom, a (CH₂)₀₋₆—NRaRb, (CH₂)₀₋₆—NH—SO₂—Rc, (CH₂)₀₋₆—NH—CO₂—Rc, (CH₂)₀₋₆—NH—CO—Rc, (CH₂)₀₋₆—NH—SO₂—NH—Rc, (CH₂)₀₋₆—NH—CO—NH—Rc, (CH₂)₀₋₆—CO₂—Rc, (CH₂)₀₋₆—SO₂—Rc, (CH₂—CO—Rc or (CH₂)₀₋₆—Rc group, Ra, Rb and Rc being as defined previously, R'₆ represents an OH, amino or alkoxy radical containing 1 to 8 carbon atoms, optionally substituted by one or more radicals chosen from the hydroxy, amino, phenylalkylamino or dialkylamino radicals, R'₂ and R'₃ represent a hydrogen atom or a methoxy radical, and G is as defined previously, the dotted lines represent an optional second bond, as well as the addition salts with acids, bases and esters.

In a second preferred group, a subject of the invention is the compounds of general formula (I) as defined previously in which $R_6$ represents an —OH, —OCH$_3$, —OCH$_2$CH$_3$, —O—(CH$_2$)$_2$—OH, —O—CH$_2$—CH(OH)—CH$_2$OH, —O—(CH$_2$)$_2$—NH$_2$, —O—(CH$_2$)$_2$—N(CH$_3$)$_2$, —NH$_2$ or —O—(CH$_2$)-phenyl group, as well as the addition salts with acids, bases and esters.

In a third preferred group, a subject of the invention is the compounds of general formula (I) as defined previously in which $R_1$ represents an S(O)$_x$—(CH$_2$)$_2$—CH(Z')—COOH group, as well as the addition salts with acids, bases and esters.

In a fourth preferred group, a subject of the invention is the compounds of general formula (I) as defined previously, in which (Z') is the (CH$_2$)$_{0-6}$—NH—CO$_2$—Rc or (CH$_2$)$_{0-6}$—NHRb group, Rb and Rc being as defined previously, as well as the addition salts with acids, bases and esters.

In a fifth preferred group, a subject of the invention is the compounds of general formula (I) as defined previously, in which (Z') is the NHCO$_2$Rc or NHRb group, as well as the addition salts with acids, bases and esters.

In a sixth preferred group, a subject of the invention is the compounds of general formula (I) as defined previously, in which Rb and Rc represent the (CH$_2$)$_{0-3}$-Ar or (CH$_2$)$_{0-3}$-Alk groups, Ar and Alk being as defined previously and being able to be substituted or non substituted, as well as the addition salts with acids, bases and esters.

In a seventh preferred group, a subject of the invention is the compounds of general formula (I) as defined previously, in which G is a group G4 of formula —NH—C(=NH)—NHRc, Rc being as defined previously, as well as the addition salts with acids, bases and esters.

In an eighth preferred group, a subject of the invention is the compounds of general formula (I) as defined previously, in which G is a group G4 of formula NH—C(=NH)—NH$_2$, as well as the addition salts with acids, bases and esters.

In a ninth preferred group, a subject of the invention is the compounds of general formula (I) as defined previously, in which G is an —NH—(Het') group as defined previously and in particular,

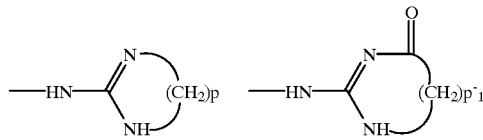

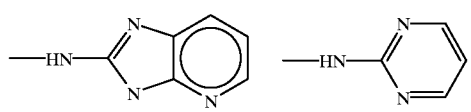

-continued

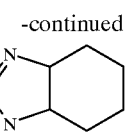

p being an integer equal to 2, 3 or 4, these heterocycles being substituted or non substituted, as well as the addition salts with acids, bases and esters.

In a tenth preferred group, a subject of the invention is the compounds of general formula (I) as defined previously, in which G is the

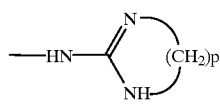

group, p being an integer equal to 2, 3 or 4, as well as the addition salts with acids, bases and esters.

In an eleventh preferred group, a subject of the invention is the compounds of formula (I) as defined previously, the names of which follow:

S- [4-[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl]-DL-homocysteine

[4-[[4-[(4,5-dihydro-1H-imidazol-2-yl)hydrazono]-9,10-dimethoxy-1,2,3,4,5,6-hexahydro-8-benz[e]azulenyl]sulphinyl]-2-[[(phenylmethoxy)carbonyl]amino butanoic acid 4-[[4-[(4,5-dihydro-1H-imidazol-2-yl)hydrazono]-9,10dimethoxy-1,2,3,4,5,6-hexahydro-8-benz[e]azulenyl]sulphonyl]-2-[[(phenylmethoxy)carbonyl]amino]butanoic acid.

A subject of the invention is also a process for the preparation of the compounds of general formula (I) comprising the following stages: a) action in the presence of a base, of a compound of formula (F1):

Hal representing a chlorine or bromine atom, Rf and Rg representing an alkyl radical containing 1 to 4 carbon atoms, on a compound of formula (II):

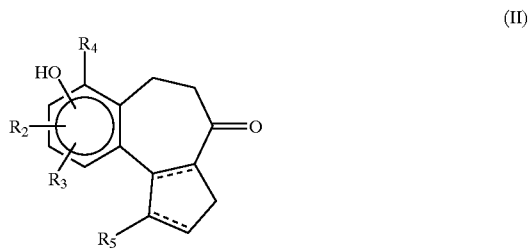

in which $R_2$, $R_3$, $R_4$ and $R_5$ are as described previously with the exception of the hydroxyl value, in order to obtain the compound of formula (IIIa):

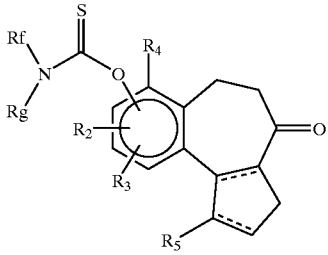

(IIIa)

b) pyrolysis of the compound of formula (IIIa) in order to obtain the compound of formula (IIIb):

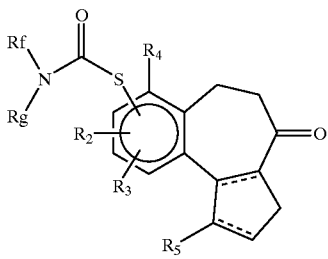

(IIIb)

c) hydrolysis in basic medium of the compound of formula (IIIb) then neutralization in order to obtain the thiol of formula (IIIc):

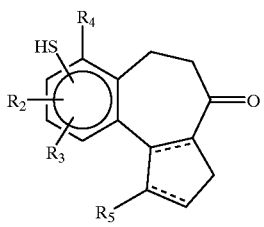

(IIIc)

d) action on the compound of formula (IIIc) of a compound of formula (F2):

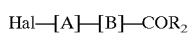

Hal—[A]—[B]—COR₂ (F2)

Hal, [A], [B] and $R_6$ being as defined previously, [B] can also represent the —CH—NHP group, P being a protective group of the amine function, in order to obtain a compound of formula (IIId):

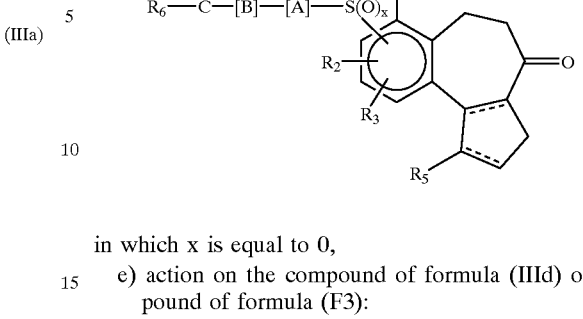

(IIId)

in which x is equal to 0,
e) action on the compound of formula (IIId) of a compound of formula (F3):

$H_2N$—G (F3)

in which G is as defined previously in order to obtain a compound of formula (IV), corresponding to the compounds of formula (I) with x=0:

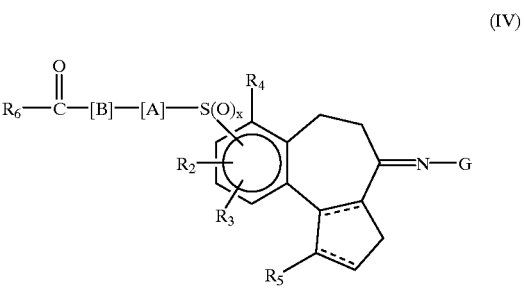

(IV)

f) compound of formula (IIId) or (IV) which is subjected if appropriate and in an appropriate order:
  to the action of a sulphur oxidizing agent, in order to obtain the compounds of formula (IIId) or (IV) with x=1 or 2,
  to the action of a base or an acid in order to detach the ester and to obtain the corresponding acid,
  to the action of a dealkylation agent,
  to the action of a deprotection agent of the NH-P function in beta position of CO—$R_6$ when [B] represents the CH—NHP group,
  to the formation of the NH—SO₂Rc, NH—CO₂R$_c$, NHCOR$_c$, NH—SO₂—NH—R$_c$, NH—CO—NHR$_c$ group from the corresponding amine in beta position of COR₆,
  to the action of an acid or a base in order to obtain the corresponding salts or to the action of an esterification agent in order to obtain the corresponding esters.

The action of the dialkylthiocarbamate halide of formula (F1) is preferably carried out according to the conditions described by M. S. Newman J. Org. Chem. 31, 3980 (1966).

The pyrolysis reaction is preferably carried out at approximately 260° C.

The hydrolysis in basic medium of the compounds of formula (IIIb) is preferably carried out in the presence of 2N soda.

The action of the compound of formula Hal—[A]—[B]—COR₆ (F2) is preferably carried out in the presence of a mineral base such as potassium carbonate or carbonate sodium in the presence of an aprotic dipolar solvent such as dimethylformamide. Hal is preferably a chlorine or bromine atom.

The action of NH$_2$—G (F3) is carried out, either without solvent, or in an alcoholic solvent such as ethanol, isopropanol or butanol. The synthon NH$_2$—G is optionally used in the form of a salt such as the hydrochloride or hydrobromide.

The saponification reaction of the ester function is carried out for example by the action of an alkaline base such as soda or potash in tetrahydrofuran or a lower alcohol such as methanol or ethanol. The ester can also be detached in acid medium according to methods known to a person skilled in the art.

The oxidization reaction of the sulphur is preferably carried out according to the method described by W. C. Stevens in Synthesis (1997) 764. The quantity of magnesium monoperoxyphtalate used will be determinant for obtaining the sulphoxide or the sulphone (0.6 ml of oxydizing agent in order to obtain the sulphoxy, 1.2 ml of oxydizing agent if one wishes to obtain the sulphone).

The oxidization reaction will preferably take place on the compound of formula (IIId), i.e. before the introduction of group G by the action of (F3) (Stage e).

The dealkylation reaction allowing access to the products of formula (I) with $R_2$, $R_3$, $R_4$ or $R_5$ representing the hydroxyls is carried out in the presence of aluminium chloride or boron tribromide.

The functionalization of NH$_2$ in alpha position of COR$_6$, [B] representing CH(NH$_2$) or CH(NH$_2$.Hcl), is carried out according to the standard methods known in organic chemistry.

The formation of NHSO$_2$R$_c$ from the corresponding amine is preferably carried out by the action of R$_c$SO$_2$Hal in the presence of a base for example triethylamine.

The formation of NHCO$_2$R$_c$ from the corresponding amine is preferably carried out by the action of R$_c$OH according to the method described in J. Org. Chem., 61, 3929–3934 after having previously reacted the triphosgene in the presence of sodium bicarbonate in order to intermediately obtain the isocyanate.

The salification reactions can be carried out under the usual conditions. For example, to salify the terminal CO$_2$H group of R$_1$, the operation is carried out in the presence of a sodium salt such as sodium carbonate or sodium or potassium acid carbonate.

Similarly, salification of the amine or the aminoguanidine which can be represented by G, with an acid, is carried out under the usual conditions. For example the operation is carried out with hydrochloric acid, for example in an ethereal solution.

The optional esterification of the products is carried out under the standard conditions known to a person skilled in the art.

In general the operation is carried out by reacting the acid of formula (I) or a functional derivative with a reagent which is capable of introducing the ester group a non-exhaustive list of which is given above in the definition of R$_6$.

The products of general formula (F1), (F2) or (F3) are known or are prepared according to methods conditions known to a person skilled in the art.

The order in which the different reagents are grafted can also be reversed, namely the compound of formula (II) is subjected to the action of compound of formula F3 in order to intermediately obtain the product of formula (IIIe):

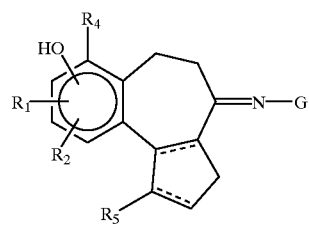

(IIIe)

which is then used in the reactions as described in Stages a), b), c), d) and if appropriate f), in order to obtain the compounds of formula (I).

In this case, if appropriate, it will be necessary to provide protection for group G of the product of formula (IIIe) then a deprotection according to methods known to a person skilled in the art (T.W. GREENE Protective Groups in Organic Synthesis. John Wiley and Sons Inc. 1991).

The deprotection reaction of the NH—P group in beta position of CO—R$_6$, [B] representing the CH—NHP group, is also carried out according to methods known to a person skilled in the art, in particular when P represents the C$_{O2}$tBu group, by a decarboxylation reaction such as for example by the action of hydrochloric acid.

Bone is constantly subjected to a dynamic process which includes bone resorption and bone formation. These processes are mediated via specialized cells. Bone formation is the result of the deposition of a mineral matrix by the osteoblasts and bone resorption is the result of the dissolution of this bone matrix by osteoclasts. Osteoporosis is characterized by a dry loss of this bone matrix. An activated mature osteoclast resorbs the bone after adhesion to the bone matrix via the secretion of proteolytic enzymes and protons inside the adhesion zone, resulting in depressions or hollows on the bone surface which appear at the time when the osteoclast detaches itself from the bone.

The compounds of formula (I) as well as their pharmaceutically acceptable addition salts have useful pharmacological properties. These compounds inhibit bone resorption which is mediated via the osteoclasts.

The compounds of the invention are thus useful in the treatment of diseases caused by the loss of bone matrix, in particular, osteoporosis, malignancy hypercalcemia, osteopenia due to bone metastasis, parodontitis, hyperparathyroidism, the periarticular erosions in rhumatoid arthritis, Paget's disease, osteopenia induced by immobilization, treatments with glucocorticoids or male or female sex hormone deficiencies.

They can also be used for the treatment of inflammatory, cancerous and cardiovascular disorders including atherosclerosis, restenosis.

Finally, they can be used as inhibitors of angiogenesis and therefore in the treatment of tumors, by inhibition of their neovascularization, diabetic retinopathies and nephropathies.

Recent studies have shown that fixation of the osteoclast to the bone is mediated by receptors: the integrins.

Integrins are a superfamilly of receptors mediating the cell/cell adhesion processes and more particularly cell/matrix, including in particular α2bβ3 as a blood platelet receptor (fibrinogen) and αvβ3 as vitronectin receptor, bone sialoproteins such as osteopontin and thrombospondin.

These receptors which are proteinic heterodimers composed of two sub-units α and β, have divalent ion fixation sites such as Ca$^{2+}$ in particular and a recognition site for their ligand predefined by the quality of their sub-units.

The αvβ3 receptor is a transmembrane glycoprotein which is expressed in a large number of cells including endothelial cells, smooth muscle cells, osteoclast and cancerous cells which thus leads to pluripotentiality of the compounds according to the invention.

The αvβ3 receptors expressed at the level of the osteoclast membrane are the basis of the adhesion/resorption process, contribute to the organisation of the cell cytoskeleton, and are involved in osteoporosis (Ross et al., J. Biol. Chem., 1987, 262, 7703).

The αvβ3 receptors expressed at the level of the smooth muscle cells of the aorta, stimulate their migration towards the neointima, which leads to the formation of atherosclerosis and the occurrence of post-angioplastic recurrence of stenosis (Brown et al, cardiovascular Res. (1994), 28, 1815).

The endothelial cells secrete growth factors which are mitogens for the endothelium and can contribute to the formation of new blood vessels (Angiogenesis). The angiogenic stimulation causes the formation of new blood vessels.

The antagonists of integrin αvβ3 can thus lead to a regression of cancerous tumors by inducing the apoptosis of the angiogenic blood vessels. (Brook et al. Cell (1994) 79, 1157).

The natural ligands of integrin αvβ3 contain all the RGD unit (Arg-Gly-Asp). The peptides containing this RGD unit as well as the anti αvβ3 anti-bodies are known for their inhibitory capacity on the resorption of dentin, obstruction of the adhesion of the osteoclasts on the mineralized matrices (Horton et al. Exp. Cell. Res. (1991), 195, 368).

The peptide Echistatin isolated from snake venom also containing an RGD unit is described as an inhibitor of the adhesion of the osteoclasts to bone, and is therefore a powerful inhibitor of bone resorption in tissues cultured in vitro (Sato et al. J. Cell. Biol. (1990), 111, 1713) and in vivo in the rat (Fisher et al. Endocrinology (1993), 132, 1441).

The compounds of formula (I) as well as their pharmaceutically acceptable addition salts and their esters can have in particular an affinity vis-à-vis the receptor of vitronectin αvβ3 or vis-à-vis other integrins having vitronectin (αvβ1, αvβ5, α2β3) for ligand by inhibiting the bond to their natural ligand.

This property thus renders the compounds of the invention of use for the prevention or the treatment of diseases the underlying pathology of which is caused by the ligands or cells which interact with the vitronectin receptor.

These compounds can also have an activity vis-à-vis other integrins which interact with their ligand via the tripeptide sequence RGD, giving them pharmacological properties which can be used for treating pathologies associated with these receptors.

This activity vis-à-vis integrins therefore renders the compounds of the invention of use in the treatment of numerous diseases such as those mentioned above or in the article by Dermot Cox DN&P 8(4) May 1995, 197–205 the content of which is included in the present Application.

Therefore a subject of the invention is the compounds of formula (I) as medicaments, as well as their pharmaceutically acceptable addition salts or their esters.

Among the medicaments according to the invention, the compounds described in the experimental part can be particularly mentioned.

Among these products, a more particular subject of the invention is, as medicaments, the compounds of formula (I) listed previously.

The dosage varies as a function of the illness to be treated and the administration route: it can vary for example from 1 mg to 1000 mg per day in an adult by oral route.

The invention extends to the pharmaceutical compositions containing at least one medicament as defined above as active ingredient.

The compounds of formula (I) are used by digestive, parenteral or local route, for example by percutaneous route. They can be prescribed in the form of plain or coated tablets, gelatin capsules, granules, suppositories, pessaries, injectable preparations, ointments, creams, gels, microspheres, nanospheres, implants, patches which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The products of formula (II), in which the hydroxy radical is in position 10, $R_2$ in position 8 and $R_3$ in position 9, represent an O-(Alk) or O—$(CH_2)_{0-3}$-Ar group, $R_4$ and $R_5$ are hydrogen atoms, are prepared according to the method described in the European Patent Application No. 0729933 and in the International Patent Application WO 97/34865 (Preparation 2).

The two other position isomers can be prepared in the following manner:

A compound of formula (IIA):

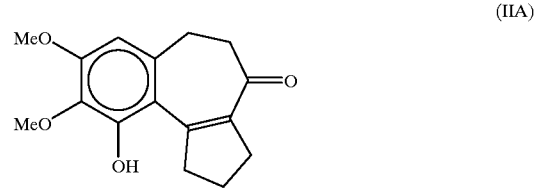

(IIA)

is subjected to the action of a dealkylation reagent, in order to obtain the compound of formula (IIB):

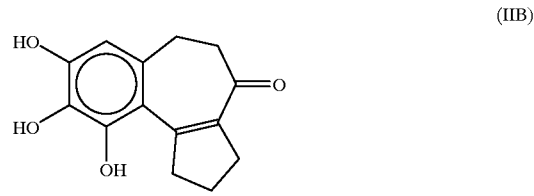

(IIB)

which compound of formula (IIB) is subjected:
  either to the action of a protective reagent of the diols in basic medium, in order to selectively obtain the product of formula (IIC):

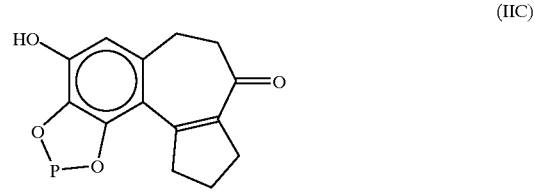

(IIC)

in which P represents the remainder of a protective reagent of the diols,
  which is successively subjected to the action of a protective 10 reagent of the phenol, of a deprotection reagent of the diols, of an alkylation agent then of a deprotection agent of the phenol in order to obtain the compound of formula (IID) corresponding to the trisubstituted product of formula (II) with OH in position 8:

(IID)

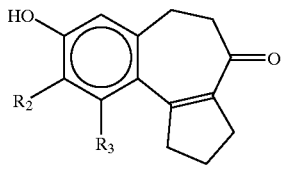

or successively to the action of a protective agent of the phenol, of an alkylation agent then of a deprotection agent in order to obtain the compound of formula (IIE) corresponding to the trisubstituted product of formula (II) with OH in position 9:

(IIE)

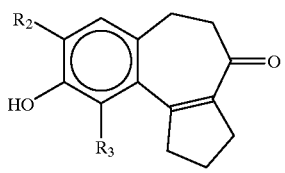

By dealkylation reagent, is preferably meant agents such as boron tribromide or aluminium chloride.

The protective reagent of the diols which is reacted on the products of formula (IIB) can be a boron derivative such as boric acid, a trialkyl borate, for example trimethyl or triethyl, or also borax.

By protective agent of the phenol, is meant in particular a halide such as mesyl or tosyl chloride or bromide or also a benzylated derivative such as benzyl tosylate or mesylate.

By deprotection reagent of the diols, is meant in particular a strong acid such as hydrochloric acid, sulphuric acid or paratoluene sulphonic acid or also an oxidizing agent, for example hydrogen peroxide, in the case of protection by a boron derivative.

By alkylation agent, is meant any standard agent known to a person skilled in the art for the alkylation of phenols. For example an alkyl halide such as methyl or ethyl chloride, an alkyl sulphate such as methyl or ethyl sulphate, or also diazomethane can be mentioned.

By deprotection agent, is meant a base such as soda, potash or also sodium or potassium carbonate.

The monosubstituted products of formula (II), in which $R_2$, $R_3$, $R_4$ and $R_5$ represent a hydrogen atom, are prepared according to a similar method to that described in the European Patent Application No. 0729933:

(i) a compound of formula (a):

(a)

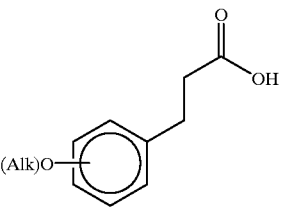

in which O-(Alk) is in meta or para position of the alkyl-carboxylic group, (Alk) being as defined previously, is subjected to the action of a halogenation agent in order to obtain the corresponding acyl halide, (ii) which is subjected to the action of a reagent of formula (b):

(b)

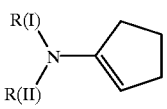

in which R(I) and R(II), identical or different represent an alkyl group containing 1 to 6 carbon atoms, or R(I) and R(II) together with the nitrogen atom to which they are linked, represent a heterocycle with 5 or 6 members, saturated or unsaturated, optionally containing another heteroatom chosen from O and N, in order to obtain a compound of formula (c):

(c)

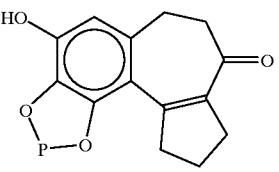

(iii) which is subjected to the action of a halogenation agent in order to obtain a compound of formula (d):

(d)

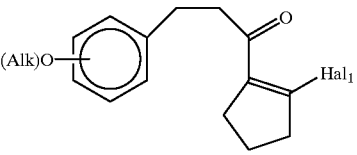

in which $Hal_1$ represents a halogen atom, (iv) which is subjected to the action of a Lewis acid, in order to obtain a compound of formula (e):

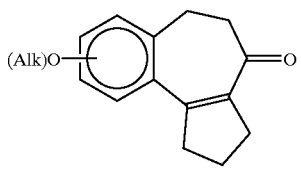

(e)

(v) which is subjected to a dealkylation reagent in order to obtain the product of formula (IIF) corresponding to the expected monosubstituted product of formula (II):

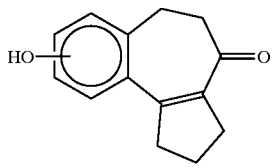

(IIF)

The disubstituted products of formula (II), in which $R_2$ represents O-(Alk) or O—$(CH_2)_{0-3}$-Ar, $R_3$, $R_4$ and $R_5$ are hydrogen atoms and OH and $R_2$ being in position 8, 9 or 10, are prepared according to the method described above starting from the compound of formula (a'):

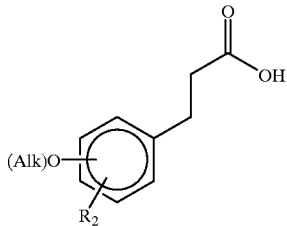

(a')

in which O-(Alk) and $R_2$ are in meta or para position of the carboxylic alkyl chain, $R_2$ being an O-(Alk) or —$(CH_2)_{0-3}$-Ar group, successively to reactions (i), (ii), (iii), (iv) and (v) and the products of formula (IIG) are obtained corresponding to the expected disubstituted products of formula (II):

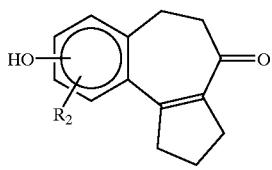

(IIG)

The halogenation agent which is reacted on the compound of formula (a) or (a') is for example thionyl chloride, oxalyl chloride or any other agent known to a person skilled in the art for preparing an acid halide.

The reagent of formula (b) is prepared starting with cyclopentanone and a secondary amine, for example diethylamine, piperidine, piperazine or, preferably, morpholine. The operation is carried out in the presence of a strong acid catalyst, for example paratoluene sulphonic acid.

The action of the enamine of formula (b) on the acid halide is preferably carried out in the presence of a tertiary amine such as triethylamine or pyridine.

The halogenation agent which is reacted on the compound of formula (c), or its disubstituted equivalent of formula (c'), can be for example thionyl chloride, phosgene, phosphorus oxychloride or, preferably, oxalyl chloride.

The Lewis acid used to cyclize the compound of formula (d), or its disubstituted equivalent of formula (d') is for example aluminium chloride, titanium tetrachloride, or preferably ferric chloride, or tin tetrachloride. The reaction, as with those above, can be carried out, for example, in a halogenated solvent such as methylene chloride, chloroform or dichloroethane.

The dealkylation reagent of the compound of formula (e), or its disubstituted equivalent of formula (e') in order to obtain the corresponding phenols is preferably aluminium chloride or boron tribromide.

The products of formula (II) in which $R_4$ is different from the hydrogen atom, are prepared by standard methods of aromatic electrophile and nucleophile substitution known to a person skilled in the art.

The products of formula (II) in which $R_5$ is different from the hydrogen atom are prepared according to methods known to a person skilled in the art and in particular according to the method described in the European Patent Application No. 0729933, i.e. by halogenation then the action of water or of an appropriate alcohol.

The products of formula (II) in which $R_5$ is a hydrogen atom and in which there is a double bond in position 1–2 are prepared according to methods known to a person skilled in the art and in particular according to the method described in the European Patent Application No. 0729933, i.e. by dehydration or dealkoxylation in an anhydrous acid medium.

The products of formula (II) in which the junction between the ring at 5 and the ring at 7 are saturated are prepared according to the standard methods of hydrogenation in particular in the presence of palladium on the carbon of the corresponding double bond.

The introduction of $R_4$, $R_5$ as well as the hydrogenation reaction is preferably carried out on the compounds of formula (IIA), (IID), (IIE), (IIF) or (IIG).

The products of formula (II) in which $R_2$ and $R_3$, in ortho position relative to each other form a ring of —O—$(CRdRe)_n$—O type as defined previously, are also prepared according to the methods known to a person skilled in the art.

A subject of the invention is also, as intermediate products, the products of formula (IIIa), (IIIb), (IIIc), (IIId) and (IIIe).

The following examples illustrate the invention without however limiting it.

EXAMPLE 1

S-[4-[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl]-DL-homocysteine Stage A: O—(9,10-dimethoxy-1,2,3,4,5,6-hexahydro-4-oxo-8-benz[e]azulenyl dimethyl carbamothioate Introduction of the O—CS—$NMe_2$ bond in position 8

45 mg of sodium hydride, then 144 mg of dimethylthiocarbamoyl chloride in 1 ml of dimethylformamide are added at 5° C. under an inert atmosphere to 2.74 g of 9,10-dimethoxy-8-hydroxy-2,3,5,6-tetrahydro-benz[e]azulen-4 (1H)-one obtained as indicated in Preparation 3 of Patent Application WO 97/34865 in 3 ml of dimethylformamide, and the reaction medium is heated for 16 hours at 80° C.

After pouring into a solution of bicarbonate and extracting with ethyl acetate and evaporating under reduced pressure, 400 mg of crude product is obtained which is purified by chromatography eluting with dichloromethane/acetone mixture 17-3. 176 mg of expected pure product is obtained.

M.p.=134–135° C.

NMR (CDCl$_3$)

| | |
|---|---|
| 1.88 (m) 2H | C$\underline{H}_2$ in position 2 |
| 2.63 (m) 2H | =C—C$\underline{H}_2$ |
| 2.75 (m) 2.86 (bs) | |
| 3.83 (s) | =C—N—Me |
| 3.48 (s) | |
| 3.83 (s) | =C—OCH$_3$ |
| 3.88 (s) | |
| 6.76 (s) | Ph—H (H in position 7) |

Stage B: S-(9,10-dimethoxy-1,2,3,4,5,6-hexahydro-4-oxo-8-benz[e]azulenyl dimethyl carbamothioate Pyrolysis 635 mg of the product obtained in the preceding stage is heated at 260° C. for 5 minutes. 475 mg of expected product is obtained. M.p.=136–137° C.

NMR (CHCl$_3$)

| | |
|---|---|
| 1.88 (m) | C$\underline{H}_2$ in position 2 |
| 4.66 (m) 2.76 (m) | =C—C$\underline{H}_2$ |
| 4.85 (m) 3.10 (m) | |
| 3.04 (bs) 3.14 (bs) | CONMe$_2$ |
| 3.82 (s) 3.86 (s) | =C—OC$\underline{H}_3$ |
| 7.16 (s) | Ph—H (H in position 7) |

Stage C: 9,10-dimethoxy-8-thiol-2,3,5,6-tetrahydro-benz[e]azulen-4(1H)-one

Hydrolysis: Obtaining the Thiol 474 mg of the product obtained in the preceding stage, 12 ml of methanol and 1 ml of 2N soda are heated under reflux for 7 hours 30 minutes, 0.5 ml of 2N soda are added and the reaction medium is heated under reflux for another 30 minutes. After adjusting the pH to 4.5 with 2N hydrochloric acid extraction is carried out, followed by washing, evaporating under reduced pressure until 500 mg of expected crude product is obtained.

Stage D: ethyl S-[9,10-dimethoxy-1,2,3,4,5,6-hexahydro-4-oxo-8-benz[e]azulenyl]-N-[(phenylmethoxy)carbonyl]-DL-homocysteinate Alkylation 500 mg of the product obtained in the preceding stage, 4 ml of dimethylformamide, 400 mg of potassium carbonate and 20 mg of 4-dimethylamino pyridine and 520 mg of ethyl 4-bromo-2-[[(phenylmethoxy)carbonyl]amino]butyrate are mixed together under an inert atmosphere and agitation is carried out overnight at ambient temperature. The reaction medium is poured into water, extracted with ethyl acetate, washed and evaporated under reduced pressure until 800 mg of crude product is obtained which is purified by chromatography eluting with a dichloromethane/ acetone mixture 18-2. 564 mg of expected pure product is obtained.

NMR (CDCl$_3$)

| | |
|---|---|
| 1.27 (t) 4.22 (q) | CO$_2$Et |
| 1.87 (m) | CH$_2$ in position 2 |
| 2.04 (m) 2.25 (m) | S—CH$_2$—C$\underline{H}_2$ of the chain |
| 2.63 (m) 2H | |
| 2.75 (m) 2H | |
| 2.81 (m) 2H | S—C$\underline{H}_2$—CH$_2$, =C—C$\underline{H}_2$ |
| 2.96 (m) 2H | |
| 3.04 (m) 2H | |
| 3.80 (s) 3.83 (s) | =C—OCH$_3$ |
| 4.51 (m) | CH$_2$—C$\underline{H}$—NH—C(O)— |
| 5.46 (bd) | CH$_2$—CH—N$\underline{H}$—C(O)— |
| 5.12 (s) | CO$_2$—C$\underline{H}$2—Ph |
| 6.81 (s) | Ph—H, H in position 7 |
| 7.35 | aromatic 5H |

Stage E: ethyl S-[4-[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl]-DL-homocysteinate Introduction of Group G 2.5 mg of isopropanol, 9 mg of monohydrated paratoluenesulphonic acid, 40 mg of 2-hydrazino-2-imidazoline hydrobromide are added to 240 mg of the product obtained in the preceding stage and agitation is carried out for 30 minutes under reflux. The reaction medium is evaporated under reduced pressure until 400 mg of crude product is obtained which is purified by chromatography eluting with a dichloroethane/methanol/ammonium hydroxide mixture 95/5/0.5. 266 mg is obtained (rf CH$_2$Cl$_2$/MeOH/NH$_2$OH= 0.25).

NMR (CDCl$_3$)

| | |
|---|---|
| 1.26 (t) 4.20 (q) | CO$_2$Et |
| 1.88 (m) | CH$_2$ in position 2 |
| 4.03 (m) 2.20 (m) | S—CH$_2$—C$\underline{H}_2$ |
| 2.70 to 3.10 (m) 10H | S—C$\underline{H}_2$ and =C—C$\underline{H}_2$ |
| 3.59 (s) 4H | N—C$\underline{H}_2$—C$\underline{H}_2$—N |
| 3.74 (s) 3.82 (s) | C$\underline{H}_3$O—C= |
| 4.49 (m,dd after exchange) | CO—NH—C$\underline{H}$— |
| 5.47 (bd mobile) | CO—N$\underline{H}$—CH— |
| 5.12 (s) | CO$_2$—C$\underline{H}_2$Ph |
| 6.76 (s) | Ph—H, H in position 7 |
| 7.35 (m) | aromatic 5H |

Stage F: S-[4-[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl]-DL-homocysteine 0.5 ml of 2N soda is added to 155 mg of the product obtained in the preceding stage in 3 ml of methanol and agitation is carried out for 1 hour 30 minutes at ambient temperature. After adjusting the pH to 5–6, by adding 0.5 to 0.6 ml of 2N hydrochloric acid, the reaction medium is evaporated under reduced pressure and the crude product is purified by chromatography eluting with a dichloromethane/methanol/ammonium hydroxide mixture 85-15-1.5. 122 mg of expected pure product is obtained.

NMR (CDCl$_3$)

| | |
|---|---|
| 1.75 to 2.10 (m) 4H | CH$_2$ in position 2, S—CH$_2$—CH$_2$ |
| 2.60 to 3.10 (m) 10H | S—CH$_2$ and CH$_2$—C= |
| 3.57 (bs) 4H | N—CH$_2$—CH$_2$—N |
| 3.69 (s) 6H | CH$_3$O—C= |
| 4.00 (m) | CH—NHCO |
| ~7.18 (m) | CH—NHCO |
| 5.02 (AB) | CO—CH$_2$—CO$_2$ |
| 6.89 (s) | Ph—H, H in position 7 |
| 7.13 to 7.40 (m) | aromatic 5H |

EXAMPLE 2

[4-[[4-[(4,5-dihydro-1H-imidazol-2-yl)hydrazono]-9,10-dimethoxy-1,2,3,4,5,6-hexahydro-8-benz[e]azulenyl]sulphinyl]-2-[[(phenylmethoxy)carbonyl] amino butanoic acid Stage A: ethyl [4-[(9,10-dimethoxy-1,2,3,4,5,6-hexahydro-4-oxo-8-benz[e]azulenyl]sulphinyl]-2-[[(phenylmethoxy)-carbonyl]amino]butanoate Oxidation 1 g of silica dioxide (0.06–0.04 m) and 0.5 ml of water are mixed together under an inert atmosphere, agitation is carried out for 20 minutes until the water is absorbed, then 2 ml of dichloromethane, 171 mg of magnesium monoperoxyphthalate, 280 mg of the product obtained in Stage D of Example 1 and also 3.6 ml of dichloromethane are added. After agitation for 3 hours at ambient temperature, the silica dioxide is separated, followed by washing, drying and evaporating under reduced pressure. 170 mg of expected product is obtained.

IR ( CHCl$_3$)

| | |
|---|---|
| =C—NH | 3426 cm$^{-1}$ |
| C=O | 1722, 1651 cm$^{-1}$ |
| C=C + | 1597, 1577, 1554, 1508 cm$^{-1}$ |
| aromatic + | |
| amide II | |
| Absorption region S=O | |

Stage B: [4-[[4-[(4,5-dihydro-1H-imidazol-2-yl)hydrazono]-9,10-dimethoxy-1,2,3,4,5,6-hexahydro-8-benz[e]azulenyl]-sulphinyl]-2-[[(phenylmethoxy)carbonyl]amino butanoic acid Introduction of G then Saponification The operation is carried out as in Stages E then F of Example 1 but starting with 160 mg of the product obtained in the preceding stage. 152 mg of expected pure product is obtained.

NMR (CDC$_{13}$)

| | |
|---|---|
| 1.65 to 2.30 (m) | CH$_2$ in position 2, S—CH$_2$—CH$_2$ |
| 2.60 to 3.20 (m) 11H | CH$_2$—C= |
| 3.57 (bs) 3.60 4H | N—CH$_2$—CH$_2$—N |
| 3.70 (s) 3.76 (s) | CH$_3$O—C= |
| 3.78 (s) 6H | |
| 3.7 to 4.1 | CH$_2$—CH—NHCO |
| 4.95 to 5.20 (m) | CO$_2$—CH$_2$Ph |
| 7.10 to 7.40 (m) 8H | Ph—H, H in position 7, aromatic H |
| 7.7 broad | mobile H. |

EXAMPLE 3

4-[[4-[(4,5-dihydro-1H-imidazol-2-yl)hydrazono]-9,10-dimethoxy-1,2,3,4,5,6-hexahydro-8-benz[e]azulenyl]-sulphonyl]-2-[[(phenylmethoxy)carbonyl] amino]butanoic acid Stage A: ethyl 4-[(9,10-dimethoxy-1,2,3,4,5,6-hexahydro-4-oxo-8-benz[e]azulenyl)sulphonyl]-2-[[(phenylmethoxy)-carbonyl]amino]butanoate The operation is carried out as in Example 2, Stage A starting with 1.10 mg of the product obtained in Stage D of Example 1 and by using 370 mg (1.2 ml) of oxidizing agent. 80 mg of expected pure product is obtained.

IR ( CHCl$_3$)

| | |
|---|---|
| NH | 3424 cm$^{-1}$ |
| C=O | 1723 cm$^{-1}$, 1655 conjugated ketone |
| aromatic + | 1600, 1578, 1508 cm$^{-1}$ |
| amide II | |
| SO$_2$ | 1307, 1142 cm$^{-1}$ |

Stage B: 4-[[4-[(4,5-dihydro-1H-imidazol-2-yl)hydrazono]-9,10-dimethoxy-1,2,3,4,5,6-hexahydro-8-benz[e]azulenyl]sulphonyl]-2-[[(phenylmethoxy)carbonyl]amino]butanoic acid The operation is carried out as in Stage B of Example 2 (introduction of G then saponification) starting with 74 mg of the sulphone obtained in the preceding stage. 76 mg of expected pure product is obtained.

NMR (CDC$_{13}$)

| | |
|---|---|
| 1.80 to 2.15 (broad m) 4H | CH$_2$ in position 2, S—CH$_2$—CH$_2$ |
| 2.84 (broad m) | CH$_2$—C= |
| 3.30 to 3.55 (m) | CH$_2$X |
| 3.60 (bs) 4H | N—CH$_2$—CH$_2$—N |
| 3.70 (s) 3.84 (s) | CH$_3$O—C= |
| 3.92 (m) | CH$_2$—CH—NHCO |
| 7.15 (broad m mobile) | CH$_2$—CH—NHCO |
| 4.99 (AB) | CO$_2$CH$_2$Ph |
| 7.34 (m) | Phenyl |
| 7.55 (s) | Ph—H, H in position 7 |
| 7.90 (sh) | mobile H. |

EXAMPLE 4

S-[4-[(2-imidazolidinylidene)hydrazono]-1,2,3,4,5,6-hexahydro-8-benz[e]azulenyl]-N-[[(phenylmethoxy)carbonyl]-DL-homocysteine Stage A: O-[1,2,3,4,5,6-hexahydro-4-oxo-8-benz[e]azulenyl]dimethylcarbamothioate 2.14 g of 8-hydroxy-2,3,5,6-tetrahydro-benz[e]azulenate (1)one prepared as indicated in Preparation 7 of Patent Application WO 97/34865 in solution in 15 ml of dimethylformamide is added dropwise to 450 mg sodium hydride. After the release of hydrogen has finished, the mixture is cooled down to 0°/+5° C. and 1.65 g of dimethylthiocarbamoyl chloride is added then the reaction medium is heated for 3 hours at 50° C.±5° C. and maintained under agitation for 16 hours at ambient temperature. Then 200 ml of a sodium bicarbonate solution at one half is poured in, followed by extracting with ethyl acetate, washing with salt water, drying, the solvents are eliminated under reduced pressure, the residue is chromatographed on silica (eluent $CH_2Cl_2$—AcOEt 95-5) and 2.45 g of expected product is recovered. M.p.=116°–118° C.

IR ( $CHCl_3$)

| | |
|---|---|
| C=O | 1640 cm$^{-1}$ |
| Conjugated System + Aromatics) | 1604, 1594, 1570, 1537, 1496 cm$^{-1}$ |

Stage B: S-[1,2,3,4,5,6-hexahydro-4-oxo-8-benz[e] azulenyl]dimethylcarbamothioate Thermic Rearrangement 2.4 g of product obtained in the preceding stage is heated to approximately 260° C. under agitation for 6 minutes. After cooling down, dichloromethane is added, followed by chromatography on silica (eluent $CH_2Cl2$-AcOEt 95/5) and 1.97 g of expected product is obtained.

IR ($CHCl_3$)

| | |
|---|---|
| C=O | 1654 cm$^{-1}$ |
| Aromatics | 1597, 1588, 1550, 1485 cm$^{-1}$ |

Stage C: 8-mercapto-2,3,5,6-tetrahydro-4-(1H)-benz[e]azulenone 100 mg of product obtained in the preceding stage is introduced into 1 ml of ethylene glycol, 0.1 ml of a solution comprising 870 mg of potash in 1 ml of water is added, followed by heating for 30 minutes under reflux, leaving the reaction medium to return to ambient temperature, adding 2N hydrochloric acid until pH: 3-4 is obtained, extracting with dichloromethane, washing with salt water and drying, the solvents are eliminated under reduced pressure and 56 mg of expected product is obtained after chromatography on silica (eluent $CH_2Cl_2$—AcOEt 97/3).

IR ($CHCl_3$)

| | |
|---|---|
| C=O | 1639 cm$^{-1}$ |
| C=C + Aromatics | 1595, 1549, 1489 cm$^{-1}$ |

Stage D: ethyl S-[1,2,3,4,5,6-hexahydro-4-oxo-8-benz[e]azulenyl]-N-[(phenylmethoxy)carbonyl]-DL-homocysteinate 1.28 g of potassium carbonate, 64 mg of 4-dimethylamino-pyridine and 1.67 g of ethyl 4-bromo-2-[[(phenylmethoxy)carbonyl]-amino]butanoate prepared in a similar manner to that of the methyl ester described in Preparation 8 of the International Patent Application WO 97/34865 is added to 738 mg of product obtained in Stage C in 10 ml of dimethylformamide.

Agitation is carried out for 40 minutes, the reaction medium is poured into 60 ml of water, extracted with ether, washed with salt water, the solvent is evaporated off under reduced pressure, the residue is chromatographed on silica (eluent $CH_2Cl_2$-acetone 98/2) and 1.46 g of expected product is obtained.

IR ($CHCl_3$)

| | |
|---|---|
| NH | 3434 cm$^{-1}$ |
| C=O | 1722 (max. complex) 1639 cm$^{-1}$ |
| Aromatics + Amide II | 1592, 1545, 1507 cm$^{-1}$ |

Stage E: ethyl S-[4-[2-imidazolidinylidene)hydrazono]-1,2,3,4,5,6-hexahydro-8-benz[e]azulenyl]-N-[(phenylmethoxy)-carbonyl]-DL-homocysteinate hydrobromide 260 mg of product obtained in Stage D in 2.5 ml of isopropanol is heated under reflux for 13 hours, in the presence of 11 mg paratoluene sulphonic acid and 115 mg of 2-hydrazino 2-imidazoline hydrobromide. The reaction medium is left to return to ambient temperature, the insoluble part is dissolved in methanol under reflux, then cooled down, the crystals are separated and 299 mg of expected product is recovered. M.p.=226–227° C.

Stage F: S-[4-[(2-imidazolidinylidene)hydrazono]-1,2,3,4,5,6-hexahydro-8-benz[e]azulenyl]-N-[(phenylmethoxy) carbonyl]-DL-homocysteine 250 mg of the product obtained in Stage E in 20 ml of methanol is agitated under reflux for 45 minutes, in the presence of 1 ml of 2N soda. The reaction medium is left to return to ambient temperature, acidified to pH 5–6 with 2N hydrochloric acid, the solvents are evaporated under reduced pressure, the residue is taken up in 100 ml of a mixture of dichloromethane/methanol 50/50, the solvents are evaporated again, the residue is chromatographed on silica (eluent $CH_2Cl_2$—MeOH—$NH_4OH$ 80/20/4) and 181 mg of expected product is recovered. M.p. ≈160° C.

NMR: (DMSO)

| | |
|---|---|
| 1.83 (m) (2H) | $CH_2$ in 9 |
| 1.94 (m) (2H) | $CH_2$ chain |
| 2.71 (bs) (4H) | the =C—$CH_2$'s |
| 2.87 (bs) (4H) | |
| 3.00 (m) (2H) | and Φ-S—$CH_2$ |
| 3.55 (bs) (4H) | the =N—$CH_2$'s |
| 3.99 (q) (1H) | =C—CH—N—C= |
| 5.02 (bs) (2H) | COO—$CH_2$-Φ |
| ≈7.13 to 7.38 (m) (8H) | Φ-C and aromatic H's |

EXAMPLE 5 hydrochloride of 4-[[4-[(2-imidazoli-dinylidene)hydrazono]-1,2,3,4,5,6-hexahydro-8-benz[e]azulenyl]sulphonyl]-2-[[(phenylmethoxy)carbonyl]amino]-butanoic acid

Stage A: ethyl 4-[[1,2,3,4,5,6-hexahydro-4-oxo-8-benz[e]azulenyl] sulphonyl]-2-[[(phenylmethoxy)-carbonyl]amino]-butanoate 2.5 ml of water is added dropwise to 5 g of silica dioxide, the reaction medium is maintained under agitation for 20 minutes, 1.05 g of magnesium monoperoxyphthalate and 25 ml of dichloromethane are added, agitation is carried out for 20 minutes, 0.31 g of the compound obtained in Stage D of Example 4 in 5 ml of dichloromethane is added, agitation is carried out for 1 hour, followed by filtering and rinsing with dichloromethane, the reaction medium is washed with a solution of sodium metabisulphite then with sodium chloride, dried, the solvents are evaporated off, the residue is chromatographed on silica (eluent $CH_2Cl_2$/acetone 95/5) and 302 mg of expected product is obtained.

IR ( $CHCl_3$)

| | |
|---|---|
| NH | 3423 cm$^{-1}$ |
| C=O | 1722–1650 cm$^{-1}$ |
| Aromatic + Amide II | 1601, 1589, 1507 cm$^{-1}$ |
| $SO_2$ | 1304, 1149 cm$^{-1}$ |

Stage B: ethyl 4-[[4-[(2-imidazolidinylidene)hydrazono]-1,2,3,4,5,6-hexahydro-8-benz[e]azulenyl]sulphonyl]-2-[[(phenylmethoxy)carbonyl]amino]-butanoate hydrobromide The operation is carried out as in Stage E of Example 4 using at the start 290 mg of product obtained in Stage A, 3 ml of isopropanol, 110 mg of 2-hydrazine 2-imidazoline hydrobromide and 10 mg of paratoluene sulphonic acid. The product obtained is chromatographed on silica (eluent $CH_2Cl_2$—MeOH—$NH_4OH$ 95/5/0.5) and 194 mg of expected product is obtained. M.p.=209–210° C.

NMR: (DMSO)

| | |
|---|---|
| 1.14 (t) | COOEt |
| 4.08 (q) | |
| ≈1.90 (m) | $CH_2$ in 9 |
| ≈2.05 (bm) | central $CH_2$ |
| 2.73 (1) (2H) | the =C—$CH_2$'s |
| 2.90 to 3.00 (6H) | |
| 3.72 (bs) | the =N—$CH_2$'s |
| 4.17 (m) (1H) | =C—CH—N—C= |
| 5.00 [AB] | COO—$CH_2$-Φ |
| ≈7.34 (1) | Φ-C |
| 7.60 (d, J=8) (1H) ) | aromatic =CH's |
| 7.75 to 7.85 (3H) | and =C—NH |
| 11.06 (bs) | mobile H's |

Stage C: hydrochloride of 4-[[4-[(2-imidazolidinylidene)hydrazono]-1,2,3,4,5,6-hexahydro-8-benz[e]azulenyl]sulphonyl]-2-[[(phenylmethoxy)carbonyl]amino]-butanoic acid The operation is carried out as in Stage F of Example 4 using at the start 248 mg of product obtained in Stage B above and 1 ml of 2N soda in 20 ml of methanol.

After adjusting to pH: 5–6, the reaction medium is concentrated to one half, separated, rinsed with water then with ice-cooled methanol, then with ether, dried at 40° C. under reduced pressure and 227 mg of crude product is obtained which is taken up in 3 ml of N hydrochloric acid, the gum formed is dissolved in methanol, the solvent is evaporated off under reduced pressure, followed by rinsing with water, drying and 208 mg of expected product is recovered.

NMR: (DMSO)

| | |
|---|---|
| 3.70 (s) | N—$CH_2$—$CH_2$—N |
| 7.60 (d, J=8) | $H_1$ |
| 7.77 (dd, J=2.8) | $H_2$ |
| 7.83 (d, J=2) | $H_4$ |
| 2.78 (m) 2H | C—$CH_2$ in position 5–6–8 and 10 |
| 2.97 (m) 6H | |
| 1.8 to 2.05 | $CH_2$ in position 9 |
| 3.28 (m) | $SO_2CH_2$ |
| 1.8 to 2.05 | the C—$CH_2$—C |
| 4.09 (m, dd, J=5.9 after exchange) | CH—N— |
| 7.67 (d, J=8.5) | mobile NH—C—O, O |
| 5.00 (AB system) | $OCH_2$C= |
| ~7.34 (m) | Φ } CBz |
| 8.25 | mobile H's |
| 21.36) | |

EXAMPLE 6

4-[[4-[(2-imidazolidinylidene)hydrazono]-1,2,3,4,5,6-hexahydro-8-benz[e]azulenyl)sulphinyl]-2-[[(phenylmethoxy)carbonyl]amino]-butanoic acid Stage A: ethyl 4-[[1,2,3,4,5,6-hexahydro-4-oxo-8-benz[e]azulenyl]sulphinyl]-2-[[(phenylmethoxy)carbonyl]amino]-butanoate The operation is carried out as in Example 5 Stage A, using at the start 1.25 g of silica dioxide, 0.63 ml of water, 210 mg of magnesium monoperoxyphthalate, 6 ml of dichloromethane and 300 mg of the compound obtained as in Example 4 Stage D, in 3 ml of dichloromethane. 217 mg of expected product is obtained.

IR ( $CHCl_3$)

| | |
|---|---|
| NH | 3425 cm$^{-1}$ |
| C=O | 1721–1647 cm$^{-1}$ |
| C=C + Aromatic + Amide II | 1599, 1588, 1508 cm$^{-1}$ |
| S->O | 1044 cm$^{-1}$ |

Stage B: ethyl 4-[[4-[4-[(2-imidazolidinylidene)hydrazono]-1,2,3,4,5,6-hexahydro-8-benz[e]azulenyl]sulphinyl]-2-[[(phenylmethoxy)carbonyl]amino]-butanoate The operation is carried out as in Example 5 Stage B using at the start 210 mg of the product obtained in Stage A, 2.2 ml of isopropanol, 88 mg of 2-hydrazine 2-imidazoline hydrobromide and 8 mg paratoluene sulphonic acid. After chromatography on silica (eluent $CH_2Cl_2$—MeOH—$NH_4OH$ 95/5/0.5), 225 mg of expected product is obtained.

IR ($CHCl_3$)

| | |
|---|---|
| NH | 3450 cm$^{-1}$ (max) |
| C=O | 1721 cm$^{-1}$ (max) |
| C=N C=C + | 1664 (sh, f), 1623 (max, F), 1544, |

| | |
|---|---|
| Aromatic + Amide II | 1506, 1488 cm$^{-1}$ |
| S->O | 1044 cm$^{-1}$ |

Stage C: 4-[[4-[(2-imidazolidinylidene)hydrazono]-1,2,3,4,5,6-hexahydro-8-benz[e]azulenyl]sulphinyl]-2-[[(phenylmethoxy)carbonyl]amino]-butanoic acid The operation is carried out as in Stage F of Example 4, using at the start 225 mg of the product obtained in Stage B, 8 ml of methanol and 1 ml of 2N soda while heating for 8 hours under reflux. 177 mg of expected product is recovered. M.p. =191–192° C.

NMR: (DMSO)

| | |
|---|---|
| 1.60 to 2.20 (m) 4H | central 2 CH$_2$'s |
| 2.65 to 3.10 (m) ~11H | the CH$_2$—O's |
| ~3.57 (broad s) ~4H | N—CH$_2$—CH$_2$—N |
| 3.96 (m) | CO—NH—CH—CH$_2$ |
| 5.00 (s) 5.01 (s) | CO$_2$CH$_2$Φ |
| 7.15 to 7.50 (m) ~8H + ethyl ether | aromatic |
| (CH$_2$SO assumed to be masked). | |

Pharmaceutical Compositions

Tablets were prepared corresponding to the following formula:

| | |
|---|---|
| product of Example 1 | 50 mg |
| Excipient (talc, starch, magnesium stearate) | 120 mg |
| QS for a tablet completed at | |

Pharmacological Study of the Products of the Invention 1—Study by the Products of the Invention of the Bond Displacement: Vitronectin/Vitronectin Receptor ($\alpha_v\beta_3$)

Protocol 96-well MaxiSorp plates are coated overnight at 4° C., with 100 µl of human Vitronectin (cf Yatohgo et al. Cell., Structure and fraction 13: 281–292 (1988)) at 2 µg/ml, (Dilution in coating buffer).

The next day, the wells are emptied and the ligands (Vitronectin) are then fixed (see fixation buffer) for 1 hour at ambient temperature under gentle agitation.

The wells are washed six times (see washing buffer), then the following are added per well and in this order:
  40 µl of incubation buffer,
  10 µl of the dilution of the product to be tested, (the products are diluted in a 50/50 mixture of DMSO-H$_2$O)
  50 µl of human $\alpha_v\beta_3$ receptor (cf Pytela et al. Methods Enzymol (1987) 144:475) (dilution in incubation buffer, adapted according to the batch of receptor and according to the ligand).

The ligand, the human $\alpha_v\beta_3$ receptor and the products to be studied are incubated for 3 hours at ambient temperature under gentle agitation.

The wells are again washed six times, then incubated for 2 hours at ambient temperature under gentle agitation, in the presence of 100 µl of 4B12-HRP antibody, anti-receptor coupled to a peroxidase (the 4B12-HRP antibody is diluted in incubation buffer. The dilution is adapted according to the batch of receptor).

The wells are then washed six times before measurement of ligand-receptor bond is carried out using a peroxidase developer kit (TMB Microwell Peroxidase Substrate System Kirkegaard: Ref. cat. 50-76-00).

This kit contains a flask A of substrate (3,3', 5,5'-tetramethylbenzidine at 0.4 g/l) and a flask B (H$_2$O$_2$ at 0.02% in Citrate/Citric acid buffer). Extemporaneously, one volume of A is mixed with one volume of B, then the reaction mixture is distributed at the rate of 100 l/well. The enzymatic reaction develops in 12' for Vitronectin/$\alpha_v\beta_3$, then its development is stopped by the addition of 100 µl of 1M phosphoric acid.

The optical density is measured at 450 nm.

Buffers
  coating buffer: 0.05 M Carbonate, NaOH pH 9.6
  fixation buffer: PBS containing 0.5% of BSA (pH 7.4)
  washing buffer: PBS containing 0.05% of Tween 20 (pH 7.4)
  incubation buffer:
    50 mM TRIS pH 7.4
    0.5% BSA
    0.05% Tween 20
    1 mM MnCl$_2$
    50 µM CaCl$_2$
    50 µM MgCl$_2$
    100 mM NaCl.

Expression of the Results

The following curve is plotted: the percentage of bond of human vitronectin as a function of the logarithm of the concentration of each product tested.

For each product the IC$_{50}$ is determined according to the following formula:

IC$_{50}$=(BO+Bmin)/2

BO=Maximum bond in the absence of any product
Bmin=Minimum bond in the presence of the highest concentration of product.

Results

| Examples | Binding competition test Vn/VR (($\alpha_v\beta_3$)) IC$_{50}$ in µM |
|---|---|
| EX. 1 | 0.040 |
| EX. 4 | 0.030 |
| EX. 5 | 0.033 |
| EX. 6 | 0.230 |

What is claimed is:

1. A compound selected from the group consisting of a compound of the formula

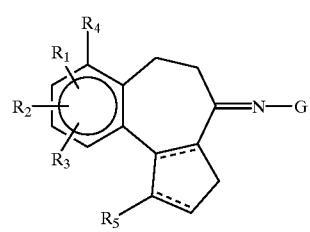

I wherein R$_1$ is —S(O$_x$—[A]—[B]—COR$_6$, x is an integer from 0 to 2, —[A]— is saturated or unsaturated acyclic divalent hydrocarbon of 1 to 12 carbon atoms, —[B]— is selected from the group consisting of phenylene, —CH(Z)— and a single bond, (Z)— is selected from the group consisting of hydrogen,

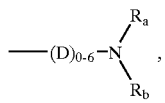

—(D)$_{0-6}$—NH—SO$_2$—Rc, —(D)$_{0-6}$—NH—CO$_2$—Rc, —(D)$_{0-6}$—NH—CO—Rc, —(D)$_{0-6}$—NH—SO$_2$—NH—R$_c$, (D)$_{0-6}$—NH—CO—NH—R$_c$, —(D)$_{0-6}$—CO$_2$—Rc, —(D)$_{0-6}$—SO$_2$—R$_c$, —(D)$_{0-6}$—CO—R$_c$ and —(D)$_{0-6}$—R$_c$, D is saturated or unsaturated acyclic divalent hydrocarbon of 0 to 6 carbon atoms, R$_a$, R$_b$ and R$_c$ are individually selected from the group consisting of hydrogen, —(CH$_2$)$_{0-3}$-Ar, —(CH$_2$)$_{0-3}$—Het and —(CH$_2$)$_{0-3}$-Alk, Ar is a carbocyclic aryl of 6 to 12 carbon atoms, Het is an aromatic or non-aromatic, saturated or unsaturated heterocyclic of 1 to 9 carbon atoms and 1 to 5 heteroatoms selected from the group consisting of oxygen, sulfur and nitrogen, Alk is a non-aromatic, saturated or unsaturated, acyclic or cyclic hydrocarbon of up to 12 carbon atoms, Het, Ar and Alk may be substituted or unsubstituted or R$_a$ and R$_b$ together with the nitrogen to which they are attached form an aromatic or non-aromatic, saturated or unsaturated, substituted or unsubstituted heterocyclic optionally containing at least one heteroatom selected from the group consisting of oxygen, sulfur and nitrogen, R$_6$ is selected from the group consisting of —OH, alkoxy of 1 to 6 carbon atoms, aryloxy of 6 to 14 carbon atoms, —NH$_2$, remainder of an L or D amino acid and —NHAlk and NH(Alk)$_2$, Alk is defined as above, R$_2$ and R$_3$ are individually selected from the group consisting of OH, —OAlk and —O—(CH$_2$)$_{0-3}$-Ar, Alk and Ar being defined as above or R$_2$ and R$_3$ together form —O—(CR$_d$R$_e$)$_n$—O—, n is an integer from 1 to 5, R$_d$, and R$_e$ are individually selected from the group consisting of hydrogen, alkyl of 1 to 6 carbon atoms and phenyl, R$_4$ is selected from the group consisting of hydrogen, halogen, —OH, —NH$_2$, —NO$_2$, —CN, —CF$_3$, acyl and acyloxy of an organic carboxylic acid of 1 to 12 carbon atoms, alkenyl and alkynyl of up to 6 carbon atoms, alkyl, alkylthio, alkoxy, alkylamino and dialkylamino and dialkylaminoalkoxy wherein the alkyl is 1 to 6 carbon atoms, R$_5$ is selected from the group consisting of hydrogen, —OH, halogen, —OAlk and —O—(CH$_2$)$_{0-3}$-Ar, Alk and Ar are as defined above, G is selected from the group consisting of

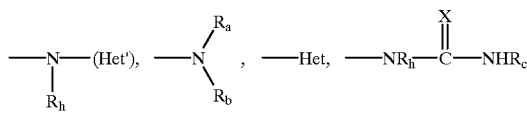

amd —NRh$_h$ —SO$_2$—R$_c$, R$_h$ is hydrogen or Alk as defined above, Het' is

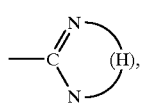

(H) with —N=C—NH— forms an aromatic or non-aromatic, substituted or unsubstituted, mono- or bicyclic heterocyclic of 1 to 9 carbon atoms and 2 to 5 heteroatoms selected from the group consisting of oxygen, sulfur and nitrogen, R$_a$, R$_b$ and R$_c$ are defined as above, X is oxygen or sulfur or nitrogen and its salts with pharmaceutically acceptable acids and bases.

2. A compound of claim 1 having the formula

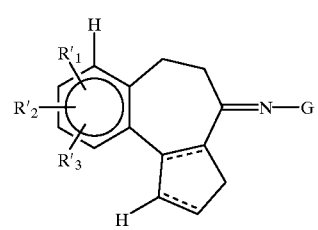

wherein R'$_1$ is —S(O)$_x$—[A']—[B']—COR'$_6$, x is 0, 1 or 2, —[A] is selected from the group consisting of alkylene, alkenylene and alkynyl of 2 to 6 carbon atoms, [B]— is a single bond or —(CH(Z)'—, Z' is selected from the group consisting of hydrogen

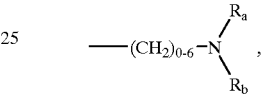

—(CH$_2$)$_{0-6}$—NH—SO$_2$—R$_c$, —(CH$_2$)$_{0-6}$—NH—CO$_2$—R$_c$, —(CH$_2$)$_{0-6}$—NH—CO—R$_c$, —(CH$_2$)$_{0-6}$—NH—SO$_2$NH—R$_c$, —(CH$_2$)$_{0-6}$—CO—NH—R$_c$, —(CH$_2$)$_{0-6}$—CO$_2$—R$_c$, —(CH$_2$)$_{0-6}$—SO$_2$—R$_c$, —(CH$_2$)$_{0-6}$—COR$_c$ and —(CH$_2$)$_{0-6}$—R$_c$, G, R$_a$, R$_b$ and R$_c$ are defined as in claim 1, R'$_6$ is selected from the group consisting of —OH, —NH$_2$ and alkoxy of 1 to 8 carbon atoms unsubstituted or substituted with at least one member of the group consisting of —OH, —NH$_2$, phenylalkylamino and dialkylamino, the alkyl being 1 to 6 carbon atoms, R'$_2$ and R'$_3$ are hydrogen or methoxy and the dotted lines are an optional double bond.

3. A compound of claim 1 wherein R$_6$ is selected from the group consisting of —OH, methoxy, ethoxy, propoxy, —O—CH$_2$—CH(OH)— CH$_2$—OH, —O—(CH$_2$)$_2$—NH$_2$, —O—(CH$_2$)$_2$—N—(CH$_3$)$_2$, —NH$_2$ and —O—(CH$_2$)-phenyl.

4. A compound of claim 1 wherein R$_1$ is —S(O)$_x$—CH$_2$ (Z')—COOH, x is 0 or 1 or 2 and Z' is selected from the group consisting of hydrogen

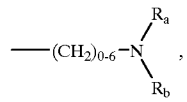

—(CH$_2$)$_{0-6}$—NH—SO$_2$—R$_c$, —(CH$_2$)$_{0-6}$—NH—CO$_2$—R$_c$, —(CH$_2$)$_{0-6}$—NH—CO—R$_c$, —(CH$_2$)$_{0-6}$—NH—SO$_2$—NHR$_c$, —(CH$_2$)$_{0-6}$—NH —CO—R$_c$, —(CH$_2$)$_{0-6}$—CO$_2$—R$_c$, —(CH$_2$)$_{0-6}$—SO$_2$—R$_c$, and —(CH$_2$)$_{0-6}$—R$_c$.

5. A compound of claim 1 wherein Z' is —(CH$_2$)$_{0-6}$—NH—CO$_2$—R$_c$ or —(CH$_2$)$_{0-6}$—NH—R$_b$.

6. A compound of claim 5 wherein Z' is —NH—CO$_2$—R$_c$ or —NHR$_b$.

7. A compound of claim 6 wherein R$_b$ and R$_c$ are —(CH$_2$)$_{0-3}$-Ar or —(CH$_2$)$_{0-3}$-Alk.

8. A compound of claim 1 wherein G is

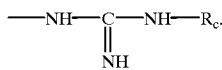

9. A compound of claim wherein $R_c$ is hydrogen.

10. A compound of claim wherein G is —NH—(Het') and Het' is defined as in claim 1.

11. A compound of claim 10 wherein G is selected from the group consisting of

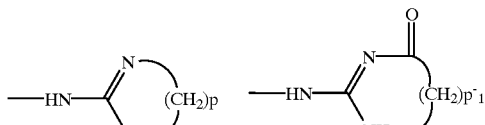

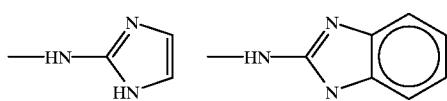

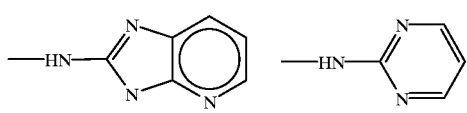

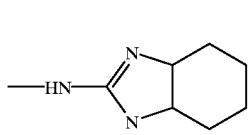

p being an integer equal to 2, 3 or 4, these heterocycles being substituted or non substituted, as well as the addition salts with acids, bases.

12. A compound of claim 10 wherein G is selected from the group consisting of

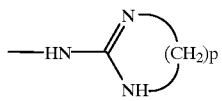

p being an integer equal to 2, 3 or 4, as well as the addition salts with acids, bases.

13. A compound of claim 1 selected from the group consisting of:

S-[4-[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl-]-DL-homocysteine

[4-[[4-[(4,5-dihydro-1H-imidazol-2-yl)hydrazono]-9,10-dimethoxy-1,2,3,4,5,6-hexahydro-8-benz[e]azulenyl] sulphinyl]-2-[[(phenylmethoxy)carbonyl]amino butanoic acid 4-[[4-[(4,5-dihydro-1H-imidazol-2-yl)hydrazono]-9,10-dimethoxy-1,2,3,4,5,6-hexahydro-8-benz[e]azulenyl] sulphonyl]-2-[[(phenylmethoxy)carbonyl]amino] butanoic acid.

14. A compound of a formula selected from the group consisting of

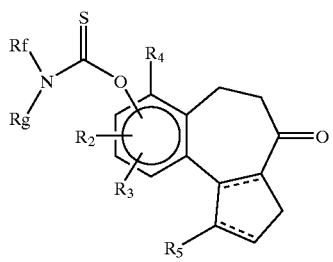

IIIa

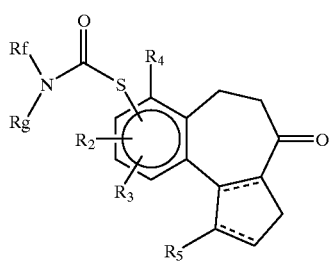

IIIb

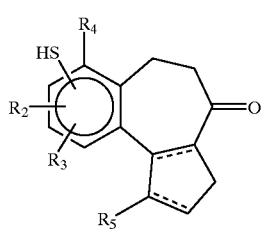

IIIc

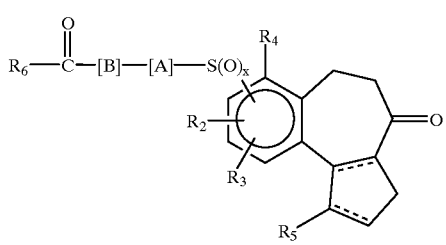

IIId

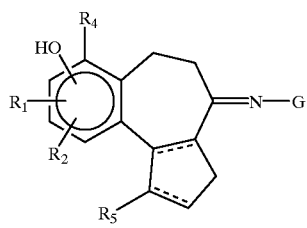

IIIe wherein $R_1$, $R_2$, $R_3$, $R_4$, $R_5$, $R_6$, A, B and G are as defined in claim 1.

15. A composition for preventing loss of bone matrix comprising an effective amount of a compound of claim 1 to treat loss of bone matrix and an inert pharmaceutical carrier.

16. A composition for preventing loss of bone matrix comprising an effective amount of a compound of claim 13 to treat loss of bone matrix and an inert pharmaceutical carrier.

17. Process for the preparation of the compounds of formula (I) as defined in claim 1, comprising the following stages:

a) action in the presence of a base, of a compound of formula (F1):

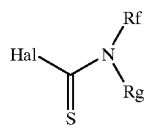
(F1)

Hal representing a chlorine or bromine atom, Rf and Rg representing an alkyl radical containing 1 to 4 carbon atoms, on a compound of formula (II):

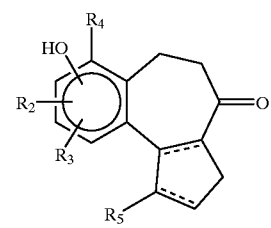
(II)

in which $R_2$, $R_3$, $R_4$ and $R_5$ are as described in claim 1, with the exception of the hydroxyl value, in order to obtain the compound of formula (IIIa):

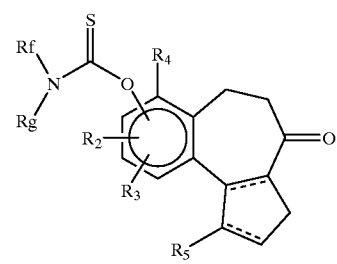
(IIIa)

b) pyrolysis of the compound of formula (IIIa) in order to obtain the compound of formula (IIIb):

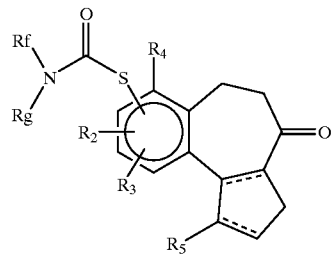
(IIIb)

c) hydrolysis in basic medium of the compound of formula (IIIb) then neutralization in order to obtain the thiol of formula (IIIc):

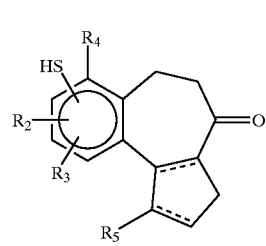
(IIIc)

d) action on the compound of formula (IIIc) of a compound of formula (F2):

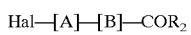
Hal—[A]—[B]—COR$_2$ (F2)

Hal, [A], [B] and $R_6$ being as defined in claim 1, [B] can also represent the —CH—NHP group, P being a protective group of the amine function, in order to obtain a compound of formula (IIId):

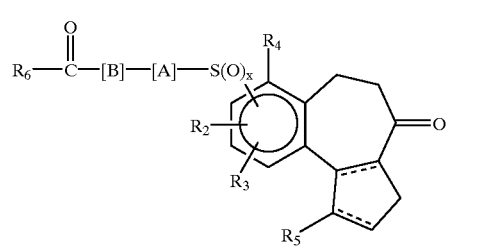
(IIId)

in which x is equal to 0, e) action on the compound of formula (IIId) of a compound of formula (F3):

H$_2$N—G (F3)

in which G is as defined in claim 1 in order to obtain a compound of formula (IV), corresponding to the compounds of formula (I) with x=0:

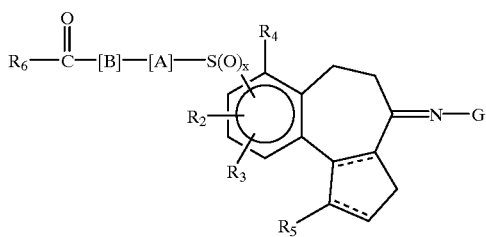
(IV)

f) compound of formula (IIId) or (IV) which is subjected if appropriate and in an appropriate order:
- to the action of a sulphur oxidizing agent, in order to obtain the compounds of formula (IIId) or (IV) with x=1 or 2,
- to the action of a base or an acid in order to detach the ester and to obtain the corresponding acid,
- to the action of a dealkylation agent,
- to the action of a deprotection agent of the NH—P function in beta position of CO—$R_6$ when [B] represents the CH—NHP group,
- to the formation of the NH—$SO_2R_c$, NH—$CO_2R_c$, NHCO$R_c$, NH—$SO_2$—NH—$R_c$, NH—CO—NH$R_c$ group from the corresponding amine in beta position of CO$R_6$,
- to the action of an acid or a base in order to obtain the corresponding salts or to the action of an esterification agent in order to obtain the corresponding esters.

18. The process of claim 17 wherein a compound of formula (II) is subjected beforehand to the action of a compound of formula (F3) in order to obtain a compound of formula (IIIe):

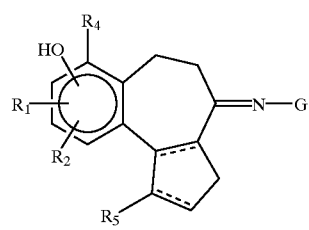
(IIIe)

which is then used in the reactions as described in stages a), b), c), d) and if appropriate f).

19. A method of preventing loss of bone matrix in warm-blooded animals comprising administering to warm-blooded animals in need thereof an amount of a compound of claim 1 sufficient to prevent loss of bone matrix.

20. A method of preventing loss of bone matrix in warm-blooded animals comprising administering to warm-blooded animals in need thereof an amount of a compound of claim 13 sufficient to prevent loss of bone matrix.

* * * * *